United States Patent [19]
Gogol, Jr. et al.

[11] Patent Number: 5,948,983
[45] Date of Patent: Sep. 7, 1999

[54] WALL DEPOSITION MONITORING SYSTEM

[75] Inventors: Carl C. Gogol, Jr., Manlius; Mark F. Kendrick, Syracuse, both of N.Y.

[73] Assignee: Leybold Inficon, Inc., E. Syracuse, N.Y.

[21] Appl. No.: 09/120,773

[22] Filed: Jul. 22, 1998

Related U.S. Application Data

[60] Provisional application No. 60/053,817, Jul. 25, 1997.

[51] Int. Cl.$^6$ ............................. G01N 29/04; B05C 11/00
[52] U.S. Cl. .............................................. 73/579; 118/664
[58] Field of Search ................................. 73/579; 118/664

[56] References Cited

U.S. PATENT DOCUMENTS

| | | | |
|---|---|---|---|
| 3,383,238 | 5/1968 | Unzicker et al. | 117/106 |
| 3,667,424 | 6/1972 | Cornelius et al. | 118/49.5 |
| 3,747,558 | 7/1973 | Harel | 118/8 |
| 4,121,537 | 10/1978 | Maruyama et al. | 118/7 |
| 4,207,836 | 6/1980 | Nonaka | 118/664 |
| 4,362,125 | 12/1982 | Schadler | 118/712 |
| 5,025,664 | 6/1991 | Kendrick et al. | 73/579 |
| 5,536,317 | 7/1996 | Crain et al. | 118/664 |

FOREIGN PATENT DOCUMENTS

| | | |
|---|---|---|
| 3206910 | 9/1991 | Japan . |
| 4154692 | 5/1992 | Japan . |

OTHER PUBLICATIONS

Article "Observations on a Quartz Crystal Deposition Monitor" by King and Hoffman.

Relevant portions of text entitled: "Introduction to Quartz Crystal Unit Design" by Virgil E. Bottom, Ph.d.

Brochure "The Hunt For High–Performance Optical Coatings" Reprinted from the Oct. 1995 issue of Photonics Spectra, Laurin Publishing Co., Inc.

*Primary Examiner*—Hezron Williams
*Assistant Examiner*—Richard A. Moller
*Attorney, Agent, or Firm*—Wall Marjama Bilinski & Burr

[57] ABSTRACT

A wall deposit monitoring system for measuring variation in wall deposit thickness in an etch or deposition chamber having a contained reactive environment includes at least one quartz or other piezoelectric crystal sensor installed through a wall of the chamber using a feed-through member. A cover assembly retains the sensor at a projecting end of the feed-through member in a position in proximity with the interior of a chamber wall. The cover includes an opening providing access to the active portion of the sensor for exposure to the reactive environment. An attached oscillating device causes the active portion of the sensor to resonate. As processing is performed in the chamber, a solid reaction product accumulates on the exposed active portion, damping the vibration of the sensor. A detection device sensing the shift in frequency can then calculate the relative change in thickness for a given material. When used with highly reactive environments, the assembly is constructed of non-reactive materials which are sufficiently electrical and thermally conductive.

8 Claims, 4 Drawing Sheets

WALL DEPOSITION MONITORING SYSTEM

CROSS REFERENCE TO RELATED APPLICATION

Reference is made to and priority claimed from U.S. Provisional Application Ser. No. 60/053,817 filed Jul. 25, 1997, entitled "Wall Deposition Monitoring System".

FIELD OF THE INVENTION

This invention relates to the field of deposition monitors, and more specifically to a monitoring system employing a quartz crystal sensor for measuring variations in wall deposit thickness in a etch or deposition chamber.

BACKGROUND OF THE INVENTION

A number of processes are known for depositing or removing thin film material onto or from a semiconductor substrate. Typically, these processes occur in a reaction (etch or deposition) chamber containing a highly reactive environment such as produced in a chemical vapor deposition (CVD) reaction between a carrier gas, such as hydrogen and a precursor, such as trimethylamine alane, or nickel pentamethylcyclopentadienyl allyl, among others, producing a solid reaction product, such as aluminum and nickel, respectively.

The resulting solid reaction product, however, produces a residue which is not only deposited onto the substrate, but on the interior of the walls of the reaction chamber, as well.

Over time, and in the course of an accumulated number of coating runs, sufficient buildup occurs produce a layer which, if unchecked, will eventually peel from the walls, and fall onto the substrate. Given the stringent specifications (on the order of $1 \times E-3$ Angstroms) for the avoidance of particles, such peeling could produce a deleterious effect.

Therefore, after a certain number of coating or etching runs, processing must be interrupted in order to clean the chamber so as to remove the deposited wall residue. Presently, empirical data is used to determine the number of coating runs which can be performed prior to a necessity to clean the chamber walls. This data, however, is highly process dependent and can easily be influenced by extraneous factors (e.g., ambient atmosphere, humidity) or a change in processing conditions. There is no current detection apparatus available for determining when the interior walls of a deposition chamber have reached a threshold thickness value.

Moreover, it has been observed that the time required to clean the chamber does not vary linearly, but varies exponentially based on the thickness of the accumulated wall residue thickness. Time is an important factor because the variation in cleaning times (3–4 hours versus 15–18 hours) can greatly increase chamber down time. There is a perceived tradeoff to put off cleaning to an intermediate time, or put differently, a wall thickness threshold, to satisfy the competing concerns to optimize cleaning and down time most efficiently. In addition, it is frequently advantageous to leave a small amount of built up wall residue to avoid changing the surface of the chamber with time as would occur if all of the material were to be removed. To date, no means have been developed for monitoring the wall thickness on a real-time basis without resorting to empirical data, or by interrupting the process by opening the chamber.

It has been found that quartz-crystal sensors, such as these manufactured by Leybold Inficon, Inc., of East Syracuse, N.Y., are capable of the high precision resolution, reliability, and accuracy required to solve the above problem and to monitor wall thickness variation in a repeatable manner. However, a system incorporating these types of sensors has not been readily feasible due to concerns relating to the corrosive and highly reactive environment found within an etch or deposition chamber, as well as competing concerns which are electrical and thermal in nature.

SUMMARY OF THE INVENTION

It is a primary object of the present invention to improve the state of the art of deposition monitoring systems.

It is another object of the present invention to provide a wall residue monitoring system which can be easily installed with respect to a deposition or etch chamber and is suitably compact.

It is another object of the present invention to provide a wall monitoring system which is made from materials which will reliably perform despite the highly corrosive and reactive environments typically found in reaction chambers.

Therefore, and according to a preferred aspect of the present invention, there is provided a monitoring system for measuring variation in wall thickness in a deposition/etch chamber having a contained reactive environment, said system including at least one quartz or other piezoelectric crystal sensor installed through a wall of the chamber using a feed-through member. A cover assembly retains the sensor at a projecting end of the feed-through member in a position in proximity with the interior of a chamber wall. The cover assembly includes a cover member having an opening providing access to an active area of the sensor which is exposed to the reactive environment and means for providing a restraining force placing the sensor in contact with a resilient member electrically attached to a detection apparatus.

An oscillator device provides a voltage which is applied across the faces of the quartz crystal sensor, causing the sensor to distort and change shape in proportion to the applied voltage. At certain discrete frequencies of the applied voltage, a condition of very sharp electromechanical resonance is encountered. When mass is applied to the active area of the quartz sensor, the frequency of the resonances is reduced. The film thickness is proportional to the frequency change, and inversely proportional to the density of film applied. When used with highly reactive environments, the components of the monitoring system are constructed of non-reactive materials which are sufficiently electrical and thermally conductive.

Preferably, the quartz crystal sensor as retained by the cover member is positioned in alignment with the opening encompassing the sensor's active area, allowing exposure to the reactive environment of the chamber and allowing accumulation of particles. In addition, the cover assembly includes resilient means for placing the electrode of the sensor in electrical contact, the resilient means including a leaf spring which assures an electrical connection and which also biases the fully coated face of the sensor into the cover member to provide a grounding path.

An advantage of the present invention is that the wall deposit thickness of a deposition or etch chamber can be easily monitored, thereby reducing the frequency of opening the chamber to interrupt in-process activity.

A further advantage of the present invention is that an accumulated threshold wall deposit thickness value or limit for cleaning or other purposes can be selected, by which the described monitoring system can automatically inform the user when this threshold limit has been reached, despite variations in processing conditions or other extraneous factors.

These and other objects, features, and advantages will become apparent from the following Detailed Description of the Invention which should be read in conjunction with the accompanying drawings.

DETAILED DESCRIPTION OF THE INVENTION

The following description relates to a monitoring system according to a specific embodiment used for measuring wall thickness variations in a specifically described deposition/etch chamber. Terms used throughout the course of discussion, such as "top", "upper", "lateral", "bottom", and the like, provide a frame of reference for the accompanying drawings, but should not be limiting as to the concepts embodying the present invention as claimed.

Figure 1:
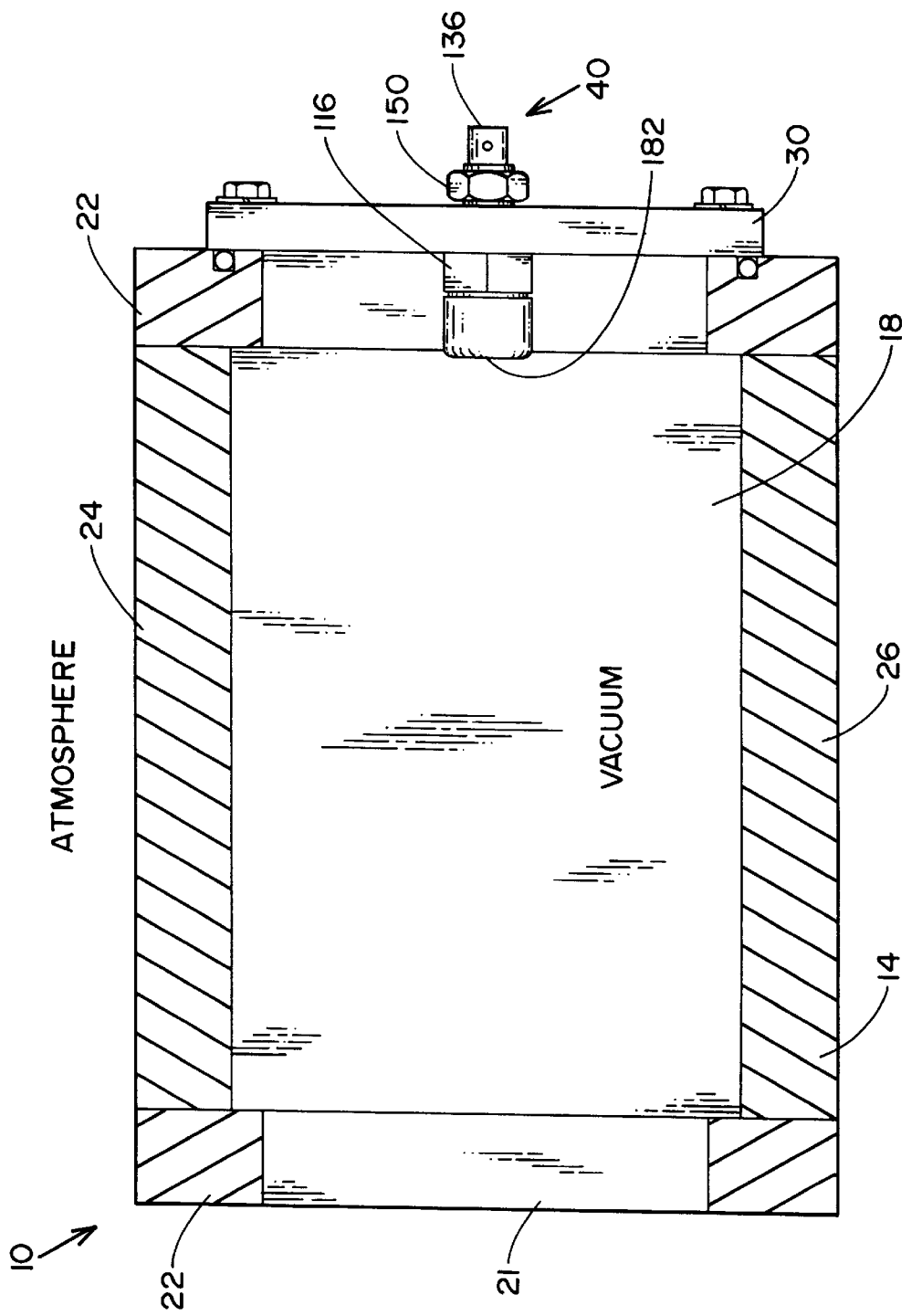
FIG. 1 is a side elevational view of a vacuum deposition/etch chamber shown in section.

Referring specifically to the drawings, and more specifically to FIG. 1, there is shown the deposition/etch chamber 10, as is commonly known in the field, used for patterning the various structures and layers of a substrate (not shown), such as a semiconductor wafer. The chamber 10 includes a housing 14 having an enclosed interior 18 defined by side walls 22, and top and bottom walls 24, 26, respectively. The chamber 10 can be one of a number of separate chambers arranged in a clustered network (not shown), or can be an individual chamber, as shown.

The substrate (not shown) is loaded and unloaded to and from the interior 18 through an opening 21 in one of the side walls 22 of the chamber 10. A carrier gas and at least one precursor(s) are separately conveyed using known supply means to the interior 18 of the chamber 10, the interior being sealed in a known manner to allow a vacuum to be applied by means (not shown) whereby the reaction between the carrier gas and the precursor causes the formation of a solid reaction product which is deposited onto the surface of the substrate. As noted above, the solid reaction product is also deposited as a thin film onto the interior of each of the side walls 22 of the chamber 10. The specific workings of the chamber, and the process reaction conducted inside, except as described, does not necessarily form an essential part of the present invention and requires no further discussion.

Still referring to FIG. 1, a wall deposition monitoring system 40 (only partially shown) in accordance with a preferred embodiment of the invention, is mounted through respective openings provided in the side wall 22 and an adjacent exterior mounting plate 30. In brief, and as detailed below, the monitoring system 40 includes a quartz or other piezoelectric crystal sensor disposed at the end of a feed-through unit which extends into the chamber interior 18. A cover assembly is used to position and retain the quartz crystal sensor in a predetermined position relative to an electrical assembly and the interior of the chamber wall, the cover also having an opening to allow access of an active surface of the sensor to the process environment. The monitoring assembly will now be described in greater detail with reference to FIG. 2.

Figure 2:
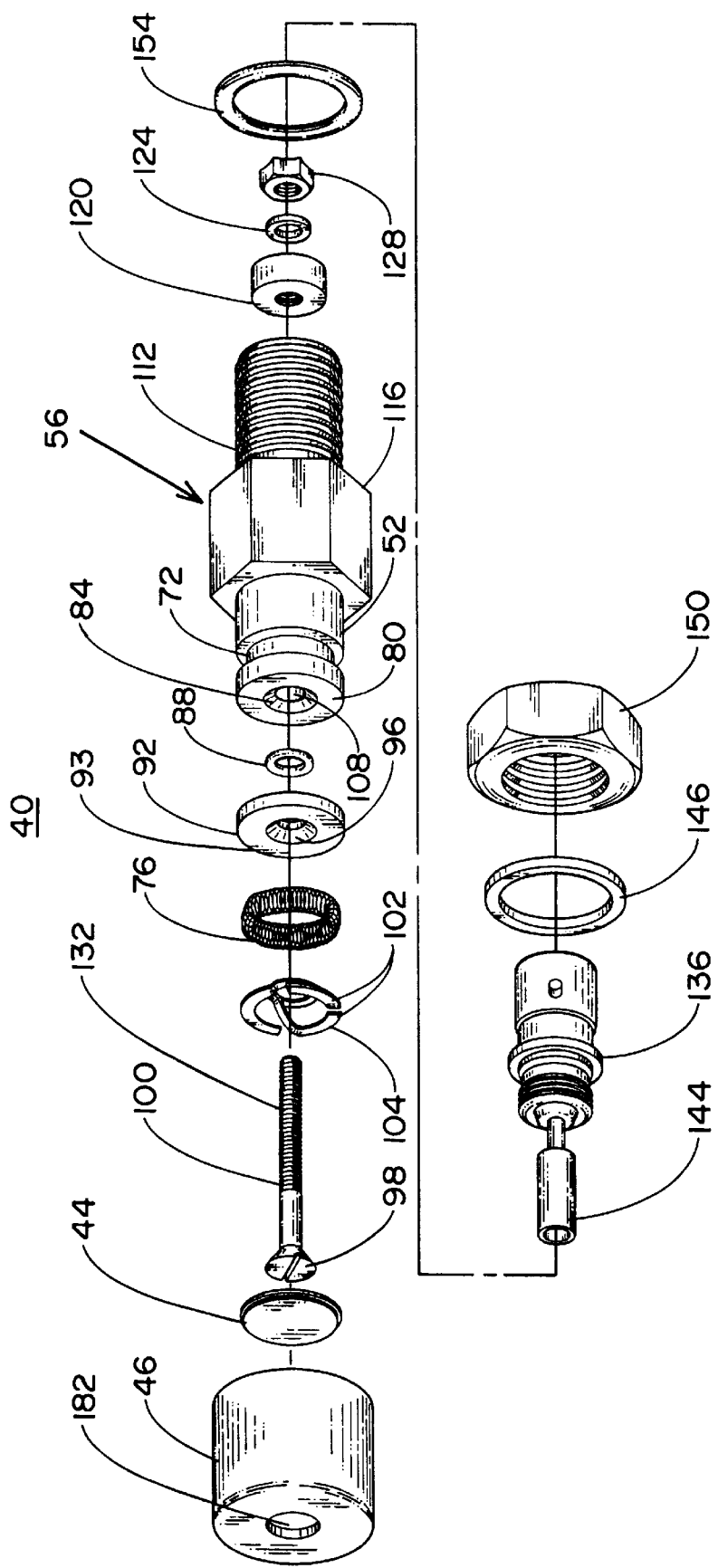
FIG. 2 is an exploded view of a chamber wall deposit monitoring system in accordance with a preferred embodiment of the present invention.

FIG. 2 provides an exploded view of the wall deposition monitoring system 40, including a disc-shaped quartz crystal sensor 44 which is positioned at a projecting end portion 52 of a feed-through member 56 and retained in a predetermined manner by a cover 46.

Figure 5:
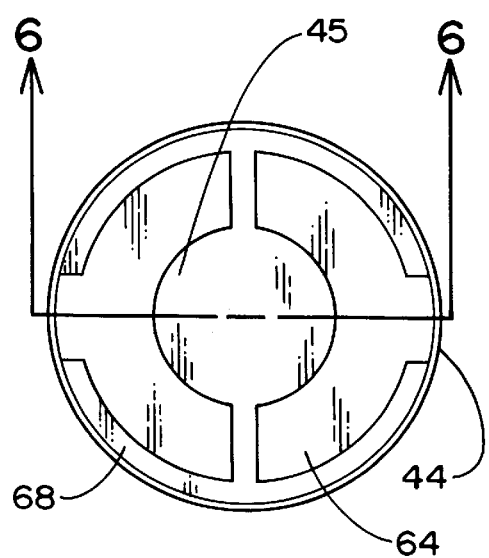
FIG. 5 is a view of the patterned side of a quartz crystal sensor used in the wall deposit monitoring system of FIGS. 2–4.
Figure 6:
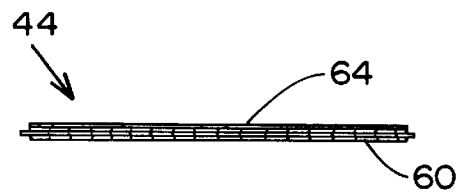
FIG. 6 is a side elevational view of the quartz crystal sensor of FIG. 5.
Figure 7:
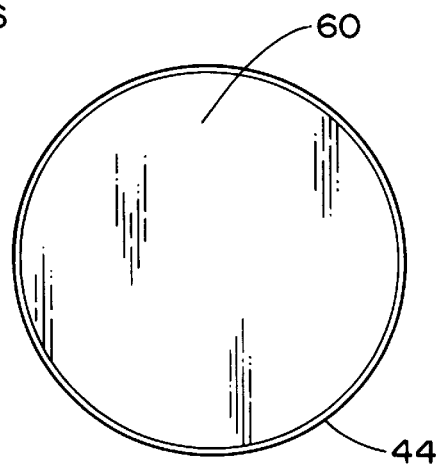
FIG. 7 is a plan view of the fully coated side of the quartz sensor of FIGS. 5 and 6.

Referring briefly to FIGS. 5–7, the quartz-crystal sensor 44 is a thin wafer-like element having a pair of opposing sides 60, 64. Each side of the sensor 44 is coated with a layer of electrically conductive material which is resistant and non-reactive with the process environment in the interior 18 of the chamber 10. Side 60 is fully coated and side 64, commonly referred to as the patterned side, is coated mainly on the outer periphery, to define an electrical contacting surface or electrode 68. Typically, the coating thickness is approximately 2000–3000 angstroms. According to the present embodiment, the sensor 44 is coated with Nickel 200. A circularly shaped active portion 45 is defined in the center of the sensor 44, which can be resonated upon application of a proper voltage. Additional details relating to the theory and manufacture of quartz-crystal sensors are commonly known to those in the field as described in the text *Introduction to Quartz Crystal Unit Design* by Virgile E. Bottom, published 1981, the entire contents of which is hereby incorporated by reference. Therefore, no additional discussion is needed, except as required, in describing the present invention.

The chamber walls 22 and mounting plate 30 of the present embodiment are each fabricated from an electrically conductive material, which is also resistant and non-reactive with the processing environment within the chamber 10. According to the embodiment, each are made from anodized aluminum, though other suitable materials can be substituted. For example, chambers which are dielectric in nature can alternately be utilized.

Referring back to FIG. 2, the projecting portion 52 of the feed-through member 56 includes a substantially cylindrical cross section with the exception of an exterior circumferential groove 72 sized for retaining a circular coil spring 76. The distal or receiving end 80 of the projecting portion 52 includes a conical countersink 84 into which a sealing O-ring 88 is encapsulated or otherwise positioned. A ceramic spacer 92 is coaxially arranged onto the distal end 80 of the projecting portion 52, the spacer also including a similar countersink 96 extending partially into the interior thereof at its distal end for retaining the head 98 of a threaded fastener 100 and a leaf spring 104 having a series of spaced fingers 102, the details of which are supplied below.

The leaf spring 104, ceramic spacer 92 and sealing O-ring 88 each include central openings which are coaxially aligned with a through opening 108 of the feed through member 56.

An exterior mounting portion of the feed-through member 56, including an exteriorly threaded end 112 is disposed opposite the projecting portion 52. A center engagement portion 116 having a hex shape allows locking engagement relative to the mounting plate 30, FIG. 1, as described in greater detail below.

The opening 108 in the feed-through unit 56 is sized to accommodate a dielectric spacer 120 made from a suitable material such as Teflon™, a split lockwasher 124, and a hex nut 128, respectively, to lock the threaded fastener 100 in place and also to compress the O-ring 88, creating a vacuum seal. The threaded end 132 of the fastener 100 is engaged by an electrical support assembly 136 at the distal end of a BNC cable 140, partially shown in FIG. 8. The support assembly 136 includes a socket 144 sized for receiving the end 132 of the threaded fastener 100. A washer 146 and jam nut 150 are fitted over the threaded portion 112 of the feed through member 56 and sealed by an O-ring 154.

Figure 3:
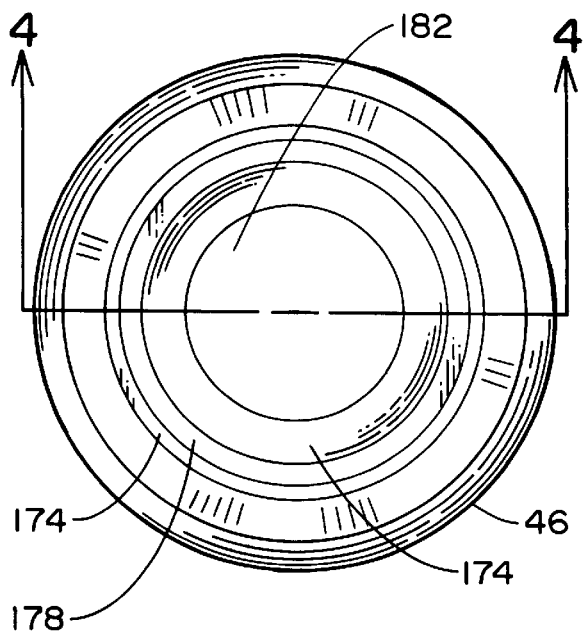
FIG. 3 is an end view of a cover used in the wall deposition monitoring system of FIG. 2.
Figure 4:
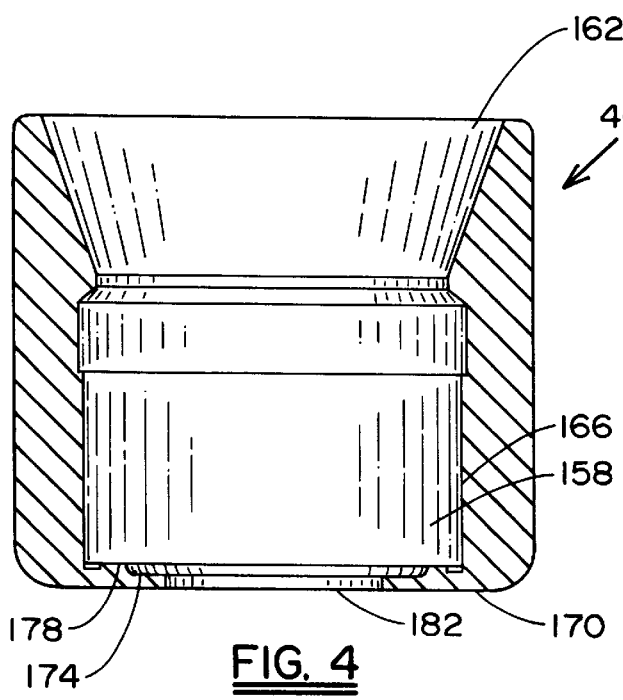
FIG. 4 is a partial side sectional view of the cover of the chamber wall deposit monitoring system of FIGS. 2 and 3.

Critical to the workings of the present invention is providing adequate support and an electrical contact for the quartz crystal sensor 44. Referring to FIGS. 2, 3, and 4, the cover 46 is an open-ended cylindrical member configured to fit over the projecting portion 52 of the feed-through member 56 and having a spaced interior 158. The interior 158 is defined by an open bottom end 162, a cylindrical inner wall 166 and a top wall 170. The interior side of the top wall 170 is recessed at portions 174 to define a circumferential shelf 178, which is configured to engage the fully coated side 60 of the quartz-crystal sensor 44, FIG. 7. A central aperture 182 of circular configuration in the center of the top wall 170, allows access to the fully coated side 60, and more specifically the active area 45 of the quartz crystal sensor 44.

Figure 8:
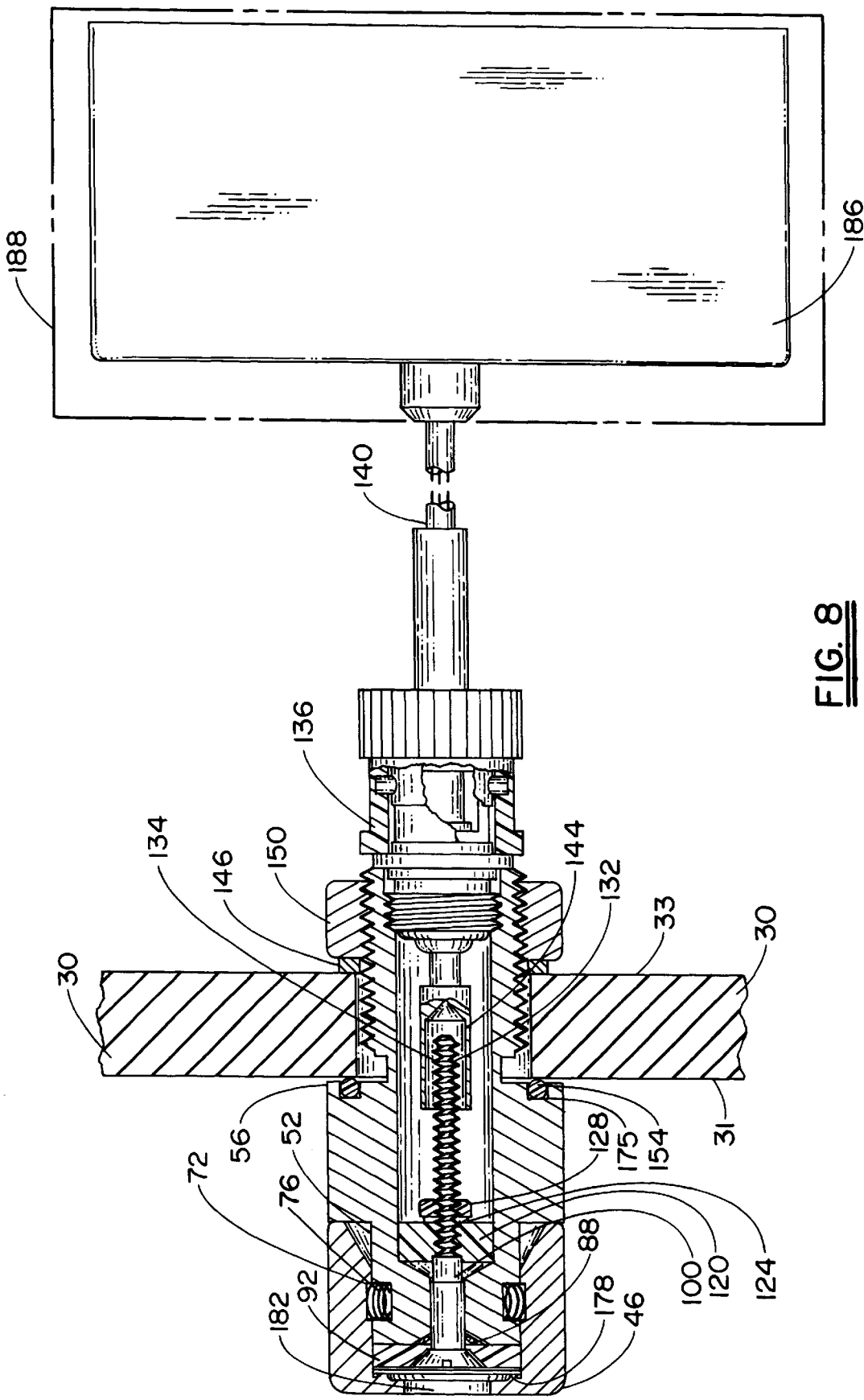
FIG. 8 is a side sectional view of the wall deposit monitoring system of FIGS. 1–4, as assembled in the wall of the deposition chamber of FIG. 1.

FIG. 8 more completely illustrates the monitoring assembly 40 as mounted to the chamber 10. Portions of the side wall 22 have been deleted for reasons of clarity.

The assembly 40 is attached to the side wall 22 by positioning the feed through unit 56 through the openings provided in the side wall and adjacent mounting plate 30. The assembly 40 is secured using the center portion 116 which engages and abuts the interior side 31 of the mounting plate 30. The jam nut 150 and associated washer 146 engage the exterior side 33 of the plate 30 to axially position the assembly 40 relative to the wall 22. Because the interior 18 of the chamber is evacuated and due to the corrosive environment therein, the O-ring 154 is preferably positioned in a circumferential groove 175 provided on the interior side 31 of the center portion 116 of the feed-through unit 56 to provide an adequate chamber vacuum seal. The O-ring 154 is made from Viton™, or can be made from any other convenient sealing material.

Because the through opening 108 in the feed-through member 56 also separates the chamber interior 18 from atmosphere, there is an additional sealing need. As noted, the O-ring 88 is positioned in the countersink 84 on the distal end 80 of the projection portion 52 of the feed-through member 56; that is, the end extending into the chamber interior 18. The O-ring 88 is encapsulated or otherwise attached within the countersink 84 and the ceramic spacer 92 is centrally placed over the distal end 80. The leaf spring 104 is then placed in the countersink 96 provided on the distal or facing side of the spacer 92, along with the fastener 100, which extends into the interior of the feed-through member 56 through the openings in the spacer into the provided opening 108 provided.

The dielectric spacer 120, the lockwasher 124, and the hex nut 128 are placed within the opposite side of the through opening 108 and over the threaded portion 132 of the attached fastener 100, whereby tightening of the hex nut 128 while using a screwdriver to hold the fastener head 98 in place supplies adequate force to compress the O-ring 88 into sealing engagement without inducing torsional forces. The head 98 of the fastener 100 is positioned in the countersink 96 and is substantially flush with the facing side 93 of the spacer 92. In this configuration, the fastener 100 is tightened into compression with the leaf spring 104 with the fingers 102 being circumferentially disposed on the facing surface 93.

The end 134 of the threaded portion 132 of the fastener 100 is fitted into the socket 144 of the electrical support assembly 136 which is sized to retain the end. The electrical support assembly 136 includes a cylindrical engagement portion adjacent the socket which is contoured to fit within an expanded portion of the through opening 108 of the feed-through member 56, the engagement portion preferably having a corresponding set of threads for engaging corresponding internal threads in the through opening. The socket 144 forms a sleeve covering the end 134 of the threaded portion 132 of the fastener 100 and establishes electrical contact therewith. As noted, the electrical contact assembly 136 is interconnected to one end of a BNC cable 140. The proximal end of the cable 140, is connected to an oscillating device 186, the details of which are known and described in U.S. Pat. No. 5,117,192, the entire contents of which are herein incorporated by reference.

Referring back to the inserted side of the monitoring assembly 40, the coil spring 76, made from an electrically conductive, environmentally resistant, and non-reactive material (Hastalloy, according to this embodiment) is inserted into the circumferential groove 72 of the projecting portion 52 and the quartz crystal sensor 44 is positioned within the interior 158 of the cover 46 and rests against the shelf 178. The cover 46 is then pressed over the projecting portion 52 of the feed-through member 56 and the protruding coil spring 76, with the open end of the cover 46 engaging the distal end of the center portion 116. When pressed into position, the cover 46 is releasably biased into position with the fingers 102 of the leaf spring 104 and the patterned side 64, and more particularly the peripheral electrode 68, is placed into intimate contact therewith. The entirety of the active area 45 of the quartz crystal sensor 44 is made accessible through the opening 182 in the cover 46. In addition, the engagement of the outer portion of the fully coated face 60 of the quartz crystal sensor 44 provides an electrical ground return point with the shelf 178, the cover 46 being preferably made of an electrically conductive material. According to the present embodiment, the feed-through unit 56, and the cover 46 are each fabricated from nickel.

In operation, and as noted the BNC cable 140 is attached at its proximal end to an oscillation generating device 186 which when powered applies a voltage through the electrical contact assembly into the socket 144, the voltage being transmitted through the conductive fastener 100 and into the leaf spring 104. The voltage is applied through the fingers 102 of the spring into the patterned side 64 and to the electrode 68. An appropriate voltage causes a sharp repeatable electromechanical resonation of the active area 45 of the quartz crystal sensor 44, e.g. 6 megahertz. A deposition sensor controller 188, shown schematically in phantom, and connected by known means to the oscillation device 186, can sense the frequency shift in the sensor based on the accumulation of mass. Knowledge of the mass density of the deposited solid product and the frequency shift produced due to the dampening of the sensor 44, FIG. 7, as film is deposited on the fully coated face 60, FIG. 7, can then be used to determine the thickness of the deposited film.

Additional details relating to the operation and theory of the deposition controller 188 is known as described in an article written by C. Gogol and C. Cipro, entitled "The Hunt for High Performance Optical Coatings," published in *Photonics Spectra,* October 1995, the entire contents of which are herein incorporated by reference.

As noted, the environment within the chamber 10 is highly reactive and corrosive, containing such highly reactive agents as fluorine and bromide, for example as found in a polysilicon etch chamber. Therefore, it is necessary that the assembly within the chamber 10 be made from materials which will not react with the on- going process or will degrade due to exposure therewith. It has been found with polysilicon etch chambers, for example, that nickel or cold rolled steel with nickel plating is preferred, including the active area 45 of the quartz crystal sensor 44.

PARTS LIST FOR FIGS. 1–8

- 10 deposition/etch chamber
- 14 housing
- 18 interior volume
- 22 side walls
- 24 top wall
- 26 bottom wall
- 30 mounting plate
- 40 wall deposition monitoring system
- 44 quartz crystal sensor
- 45 active area
- 46 cover
- 52 projecting portion
- 56 feed-through member
- 60 fully coated face side
- 64 patterned side
- 68 electrode
- 72 circumferential groove
- 76 circular coil spring
- 80 distal end
- 84 countersink
- 88 O-ring
- 92 spacer
- 93 facing side
- 96 countersink
- 98 head
- 100 threaded fastener
- 102 fingers
- 104 leaf spring
- 108 opening
- 112 threaded portion
- 116 center portion
- 120 spacer
- 124 lockwasher
- 128 hex nut
- 132 threaded end
- 136 electrical support assembly
- 140 BNC cable
- 144 socket
- 146 washer
- 150 jam nut
- 154 O-ring
- 158 cover interior
- 162 open end
- 166 inner wall
- 170 top wall
- 174 recesses
- 175 groove
- 178 circumferential shelf
- 182 access opening
- 186 oscillator device
- 188 deposition sensor controller Though the invention has been described in terms of a single preferred embodiment, it will be readily apparent that variations and modifications can be made within the spirit and scope of the invention as defined by the appended claims.

We claim:

1. A wall deposit monitoring system for measuring variations in deposit thickness in a deposition/etch chamber having an interior with a contained reactive environment, said monitoring system comprising:

at least one quartz crystal sensor installed through a wall of said reaction chamber, said at least one sensor being attached to a projecting end of a feed through member extending into said chamber interior; and a cover assembly disposed within said chamber, said cover assembly including a cover member having means for retaining said at least one piezoelectric crystal sensor at said projecting end of said feed-through member in a position in close proximity with the interior of said chamber wall.

2. A wall deposit monitoring system as recited in claim 1, wherein said cover member includes an opening accessing the environment of the chamber interior to an active area of said at least one sensor.

3. A wall deposit monitoring system as recited in claim 2, wherein said cover assembly includes means for placing a restraining force on said at least one piezoelectric crystal sensor, said system further including a resilient member onto which said at least one sensor is caused to contact by said restraining means, said resilient member being electrically attached to a detector.

4. A wall deposit monitoring system as recited in claim 1, including means for determining the resonant frequency of said at least one piezoelectric crystal sensor.

5. A wall deposit monitoring system as recited in claim 4, including means for determining the change in resonant frequency due to accumulation of material onto the active area of said at least one piezoelectric crystal sensor.

6. A wall deposit monitoring system as recited in claim 5, wherein said means for determining the resonant frequency of said at least one piezoelectric crystal sensor includes means for oscillating said at least one sensor.

7. A wall deposit monitoring system as recited in claim 4, including means for determining the period of oscillation or frequency of said at least one piezoelectric crystal sensor.

8. A wall deposit monitoring system as recited in claim 1, wherein said at least one piezoelectric crystal sensor is quartz.

* * * * *